United States Patent [19]

Storz

[11] 4,167,939

[45] Sep. 18, 1979

[54] METHOD OF TREATING PATIENTS WITH RECTOSCOPES

[76] Inventor: Karl Storz, Auf dem Schildrain 39, 72 Tuttlingen, Fed. Rep. of Germany

[21] Appl. No.: 747,591

[22] Filed: Dec. 20, 1976

[30] Foreign Application Priority Data

Jun. 11, 1976 [DE] Fed. Rep. of Germany ....... 2626179

[51] Int. Cl.² .............................................. A61B 1/00
[52] U.S. Cl. ......................................... 128/4; 128/348
[58] Field of Search ............... 128/5, 6, 7, 8, 4, 214.4, 128/347, 348, 350 R, 351, 303.15; 27/24, 25 R, 25 A

[56] References Cited

U.S. PATENT DOCUMENTS

| | | | |
|---|---|---|---|
| 2,888,017 | 5/1959 | Wallace | 28/303.15 |
| 3,071,129 | 1/1963 | Wasserman | 128/6 |
| 3,653,388 | 4/1972 | Tenckhuff | 128/350 R |
| 3,677,244 | 7/1972 | Hassinger | 128/214.4 |
| 3,871,358 | 3/1975 | Fukuda et al. | 128/2 M |

FOREIGN PATENT DOCUMENTS

| | | | |
|---|---|---|---|
| 154241 | 9/1938 | Austria | 128/5 |
| 2339928 | 8/1972 | Fed. Rep. of Germany | 128/4 |
| 587674 | 1/1959 | Italy | 128/4 |
| 533382 | 11/1976 | U.S.S.R. | 128/350 R |

*Primary Examiner*—Robert W. Michell
*Assistant Examiner*—Arthur S. Rose
*Attorney, Agent, or Firm*—Eugene M. Eckelman

[57] ABSTRACT

A divisible outer tube for a rectoscope is provided which can be opened up for removing the rectoscope therefrom during an examining procedure, such structure maintaining air tightness for ballooning the intestines and also maintaining convenience for working in combination with a colonoscope. A bayonet joint is provided between the rectoscope and the outer tube for releasable connection.

1 Claim, 4 Drawing Figures ptions on the rectoscope and/or on the divisible outer tube.

The method for using the rectoscope according to the invention preferably comprises the rectoscope firstly being used for examining the rectum, accompanied by ballooning with air, and then detaching the divisible outer tube from the rectoscope and removing the latter whereupon a colonoscope can be inserted in the divisible tube. The divisible tube is then removed.

Further advantages and details of the invention can be gathered from the following description of an embodiment with reference to the drawings.

DETAILED DESCRIPTION OF A PREFERRED EMBODIMENT

Figure 1:
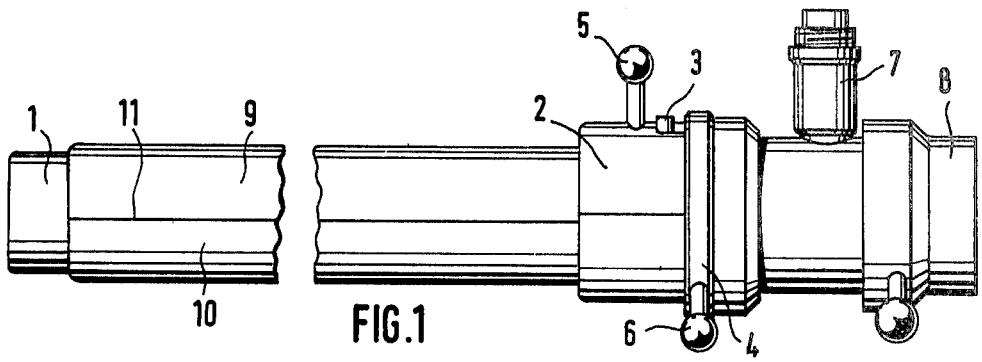
FIG. 1 is a foreshortened elevational view showing a rectoscope and a divisible outer tube of the invention mounted thereon.

FIG. 1 shows a rectoscope 1 the inner construction of which is conventional and need not therefore be described in detail. This substantially comprises a pipe having a connection 7 for a flexible photoconductor and a further connection for compressed air, not shown. In FIG. 1, the distal end is to the left and the proximal end 8 to the right, the latter end being provided with an eyepiece to permit observation by the doctor.

According to the invention, the rectoscope is encased by a divisible outer tube or auxiliary body portion 2 comprising an upper half 9 and a lower half 10. The dividing line 11 is located in the longitudinal direction of the instrument.

Figure 2:
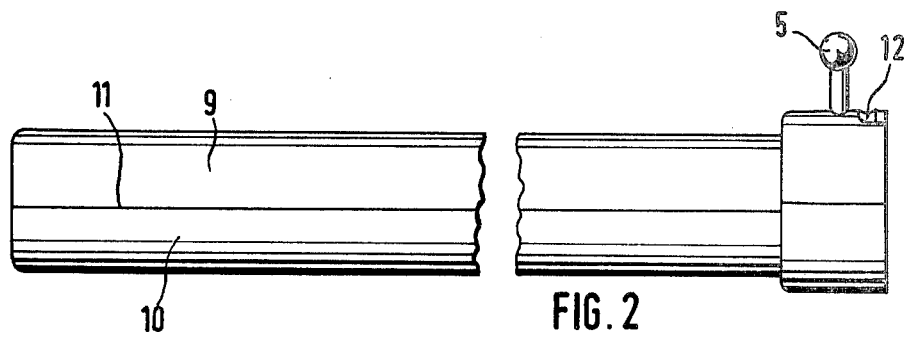
FIG. 2 is a foreshortened elevational view of the outer tube only.

FIG. 2 shows the divisible outer tube only. The two dish-shaped halves 9 and 10 can be separated by a brief axial and relative displacement of the parts. Corresponding matching tongues and grooves are provided at the distal and proximal ends to accomplish such connection and displacement. This need not be shown in detail because such divisible outer tubes are known per se. For the purposes of the invention, a groove 12 of a bayonet joint is provided in the vicinity of a finger engaging projection 5 at the proximal end, and a pin 3 on the rectoscope 1 fits into such joint. Pin 3 is on a bayonet ring 4 which is used to connect the divisible outer tube 2 with rectoscope 1 and which has a finger engaging projection 6 adapted to be gripped simultaneously with projection 5 for attaching and detaching parts 1 and 2 at the bayonet joint.

Figure 3:
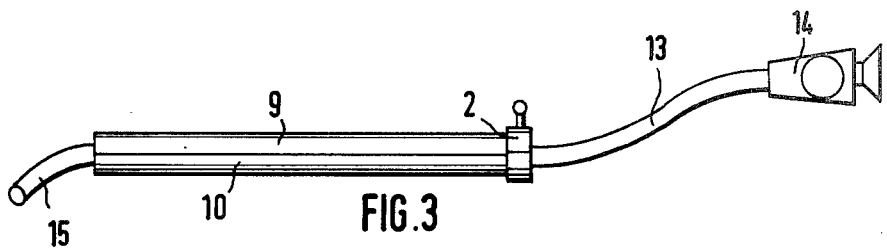
FIG. 3 is an elevational view of the outer tube with a colonoscope inserted.

According to FIG. 3, a colonoscope 13 can be inserted into tube 2 and has a head 14 which is much larger than the flexible colonoscope 13. There is no need to describe and present in detail colonoscope 13, 14 because such instruments are known per se.

Figure 4:
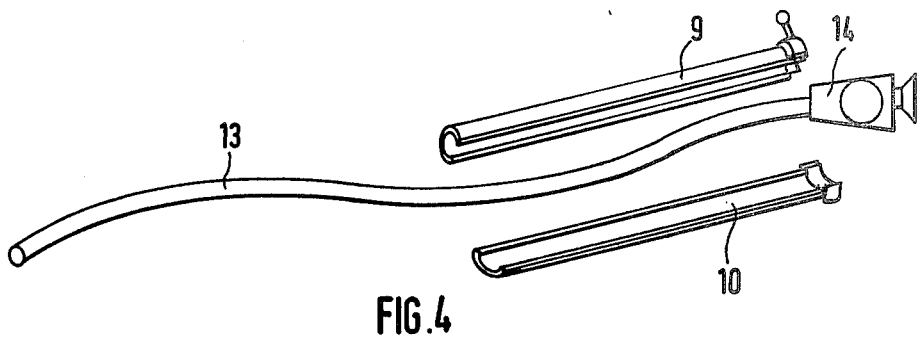
FIG. 4 is a view similar to FIG. 3 but showing the components of the divisible outer tube detached from one another.

FIG. 4 shows the two parts 9 and 10 of the divisible outer tube 2 in the detached state. In this condition, they can be removed from within the body cavity past the head 14 of the colonoscope.

The subject matter of the invention functions as follows:

The fitted rectoscope with the outer tube thereon as shown in FIG. 1 permits the examination of the rectum accompanied by ballooning with air in the known manner. The bayonet joint 3, 4 is then disconnected and the rectoscope 1 is removed from tube 2, whilst leaving the latter in the body cavity. Colonoscope 3 can then be inserted into tube 2 until the distal end 15 is out of the distal end of tube 2 in the desired manner. Through a longitudinal displacement of the two parts 9 and 10 of the tube 2 relative to one another, it is then possible to detach the two halves so that they can be removed separately from one another according to FIG. 4.

The invention leads to the advantage that the known procedure can also be used when examination is to take place accompanied by ballooning by air because the rectoscope 1 is completely airtight and can be removed from tube 2.

Having thus described my invention, I claim:

1. A method of treating a patient with a rectoscope and a colonoscope, the rectoscope having a divisible outer tube removably mounted thereon, comprising initially inserting the rectoscope with the outer tube thereon into a body cavity to examine the cavity accompanied by ballooning by air, then detaching the rectoscope from said divisible outer tube and removing the rectoscope from the body cavity while leaving the divisible tube within the cavity, introducing a portion only of the length of the colonoscope into the divisible tube, and then removing the divisible tube with the colonoscope left in the cavity.

* * * * *